United States Patent
Schmidt et al.

(10) Patent No.: US 12,424,312 B2
(45) Date of Patent: Sep. 23, 2025

(54) CONTEXT-ENHANCED MAGNETIC RESONANCE (MR) WORKFLOW ANALYSIS AND IMAGE READING

(71) Applicant: KONINKLIJKE PHILIPS N.V., Eindhoven (NL)

(72) Inventors: Joachim Dieter Schmidt, Hamburg (DE); Thomas Erik Amthor, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 78 days.

(21) Appl. No.: 17/919,370

(22) PCT Filed: Apr. 25, 2021

(86) PCT No.: PCT/EP2021/060765
§ 371 (c)(1),
(2) Date: Oct. 17, 2022

(87) PCT Pub. No.: WO2021/219521
PCT Pub. Date: Nov. 4, 2021

(65) Prior Publication Data
US 2023/0207112 A1    Jun. 29, 2023

Related U.S. Application Data

(60) Provisional application No. 63/018,672, filed on May 1, 2020.

(51) Int. Cl.
*G16H 40/40* (2018.01)
*G06V 20/40* (2022.01)
(Continued)

(52) U.S. Cl.
CPC ............. *G16H 40/40* (2018.01); *G06V 20/44* (2022.01); *G06V 20/46* (2022.01); *G06V 40/20* (2022.01);
(Continued)

(58) Field of Classification Search
CPC ........ G16H 40/40; G16H 30/20; G16H 30/40; G16H 40/63; G06V 20/44; G06V 20/46; G06V 40/20; G11B 27/34
See application file for complete search history.

(56) References Cited

U.S. PATENT DOCUMENTS 5,545,993 A     8/1996  Taguchi et al.
2009/0092953 A1* 4/2009 Yang ...................... G09B 19/24
                                                  434/219
(Continued)

OTHER PUBLICATIONS

International Search Report and Written Opinion of PCT/EP2021/060765 dated Jul. 28, 2021.

*Primary Examiner* — Dramos Kalapodas
(74) *Attorney, Agent, or Firm* — Larry Liberchuk (57) ABSTRACT

A non-transitory computer readable medium (26) stores instructions readable and executable by at least one electronic processor (20) to perform a method (100) of maintaining a machine log (30) for a medical imaging device (2). The method includes: extracting event annotations (38) from video (17, 18) acquired by at least one video camera (12, 16) positioned to image an examination region of the medical imaging device and/or an imaging bay (3) containing the medical imaging device, the event annotations representing activities occurring during a medical imaging examination performed using the medical imaging device; and recording machine log entries (32) in the machine log of the medical imaging device wherein the machine log entries are generated by the medical imaging device. The recording includes matching the extracted event annotations with machine log (Continued)

entries based on timestamps (40) of the event annotations and timestamps (34) of the machine log entries and annotating the machine log entries with the matched event annotations.

19 Claims, 3 Drawing Sheets

(51) Int. Cl.
  *G06V 40/20* (2022.01)
  *G11B 27/34* (2006.01)
  *G16H 30/20* (2018.01)
  *G16H 30/40* (2018.01)
(52) U.S. Cl.
  CPC ............. *G11B 27/34* (2013.01); *G16H 30/20* (2018.01); *G16H 30/40* (2018.01)

(56) References Cited

U.S. PATENT DOCUMENTS

| | | | | |
|---|---|---|---|---|
| 2014/0000609 | A1* | 1/2014 | Steinhauer | G16H 40/67 |
| | | | | 128/204.23 |
| 2015/0033073 | A1* | 1/2015 | Yang | A61B 5/743 |
| | | | | 714/15 |
| 2016/0262663 | A1 | 9/2016 | Maclaren et al. | |
| 2018/0314891 | A1* | 11/2018 | Ota | G16H 40/63 |
| 2019/0065763 | A1* | 2/2019 | Berg | G06F 16/9558 |
| 2020/0342968 | A1* | 10/2020 | Avinash | G16H 50/30 |
| 2020/0395105 | A1* | 12/2020 | Koby | G06V 20/20 |
| 2021/0090694 | A1* | 3/2021 | Colley | G16B 30/00 |

\* cited by examiner

CONTEXT-ENHANCED MAGNETIC RESONANCE (MR) WORKFLOW ANALYSIS AND IMAGE READING

CROSS-REFERENCE TO PRIOR APPLICATIONS

This application is the U.S. National Phase application under 35 U.S.C. § 371 of International Application No. PCT/EP2021/060765, filed on Apr. 25, 2021, which claims the benefit of U.S. Provisional Patent Application Ser. No. 63/018,672, filed May 1, 2020. This application is hereby incorporated by reference herein.

The following relates generally to the imaging arts, imaging assistance arts, imaging device maintenance arts, imaging device machine log arts, contrast injection arts, and related arts.

BACKGROUND

Existing medical imaging systems store log data drawn from the imaging device itself, which includes information such as imaging device settings and scan sequence information. The acquired images are stored to a Picture Archiving and Communication System (PACS), and can be tagged in Digital Imaging and Communications In Medicine (DICOM) format with portions of this information (e.g. certain scan settings). The machine logs may be used in retrospective workflow analysis for various purposes (quality control assessment, maintenance, etc.). The DICOM tags on the images may be referenced by the radiologist when reading a radiology examination.

While the machine logs and DICOM data are useful, they provide incomplete information, as they do not inform as to human activity during the imaging.

The following discloses certain improvements to overcome these problems and others.

SUMMARY

In one aspect, a non-transitory computer readable medium stores instructions readable and executable by at least one electronic processor to perform a method of maintaining a machine log for a medical imaging device. The method includes: extracting event annotations from video acquired by at least one video camera positioned to image an examination region of the medical imaging device and/or an imaging bay containing the medical imaging device, the event annotations representing activities occurring during a medical imaging examination performed using the medical imaging device; and recording machine log entries in the machine log of the medical imaging device wherein the machine log entries are generated by the medical imaging device. The recording includes matching the extracted event annotations with machine log entries based on timestamps of the event annotations and timestamps of the machine log entries and annotating the machine log entries with the matched event annotations.

In another aspect, an apparatus for maintaining a machine log for a medical imaging device includes at least one video camera positioned to image an examination region of the medical imaging device and/or an imaging bay containing the medical imaging device. At least one electronic processor is programmed to: extract event annotations from video acquired by the at least one video camera, the event annotations representing activities occurring during a medical imaging examination performed using the medical imaging device; record machine log entries in the machine log of the medical imaging device wherein the machine log entries are generated by the medical imaging device; match the extracted event annotations with machine log entries based on timestamps of the event annotations and timestamps of the machine log entries; and annotating the machine log entries with the matched event annotations.

In another aspect, a method of maintaining a machine log for a medical imaging device includes: acquiring video of a patient during a medical imaging examination; acquiring video of one or more medical personnel during the medical imaging examination; extracting event annotations from the acquired videos, the event annotations representing activities occurring during a medical imaging examination performed using the medical imaging device; recording machine log entries in the machine log of the medical imaging device wherein the machine log entries are generated by the medical imaging device; matching the extracted event annotations with machine log entries based on timestamps of the event annotations and timestamps of the machine log entries; and annotating the machine log entries with the matched event annotations.

One advantage resides in acquiring context information about an imaging examination and linking this information to log files.

Another advantage resides in acquiring video or images of a patient during an imaging examination and integrating this information with machine log files.

Another advantage resides in integrating information from video or images of medical personnel during an imaging examination with machine log files in a manner that facilitates efficient subsequent use of the information (for example, without requiring the reviewer to watch extensive video content).

Another advantage resides in integrating information from video or images of medical personnel during an imaging examination with machine log files in a compact manner that does not excessively increase data storage requirements for the machine log files.

Another advantage resides in matching timestamps of acquired information of a medical imaging examination with machine log entries of the medical imaging examination.

Another advantage resides in extracting event information from acquired video of a medical imaging examination without first storing the video.

Another advantage resides in extracting event information from acquired video of a medical imaging examination and then immediately deleting the video.

Another advantage resides in matching timestamps of acquired information of a medical imaging examination with images acquired during the medical imaging examination.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

In some embodiments disclosed herein, cameras can be installed to monitor the imaging examination region (e.g., a "bore" camera) and the imaging bay (e.g. a "bay" camera). The bore camera provides information about patient motion or other events relating to the patient during the imaging process, while the bay camera provides information about activities of the imaging technologist during the imaging process. Patient loading/unloading may also be captured by one or both cameras, depending on their positioning.

The video captured by the cameras in some embodiments is contemplated to be stored in the machine log and/or in the PACS along with the images. However, this approach requires extensive storage space, and would not be convenient for the use in review as the workflow analyst or radiologist would need to watch the pertinent video, which would be tedious and time consuming.

To address this, in preferred embodiments, event extraction is performed on the video streams to extract events of interest, such as detected patient motion, breath-holds, presence of a person (other than the patient) in the imaging bay, total patient loading (or unloading) time, or so forth. Each event is timestamped (e.g., beginning/end times) and may optionally be further quantified or labeled (e.g. type/amplitude of movement, number of persons in the imaging bay, positions of persons in the imaging bay, etc.).

The resulting events are stored in the machine log. Existing machine logs store timestamped events in time sequence, so the video-extracted events can be inserted as additional event entries based on the time stamps. Although not done in the illustrative examples, it is also contemplated to store in the machine log a short video segment (or a hyperlink to the video segment stored elsewhere) that captures all or a portion of the video-extracted event (or of certain events, such as a patient movement during image acquisition) for later review.

In embodiments in which the video-extracted events are stored in the PACS, typically only events relating to the patient during the actual image acquisition are of interest, and these are usually acquired by the bore camera. Events of interest include patient motion and breath-holds, for example. The events may be associated to images by timestamp and annotated to the associated images as DICOM metadata. Additionally or alternatively, the events may be stored as a separate "bore cam" file in the examination record written to the PACS. Again, it is contemplated that the events stored in the PACS may include or be hyperlinked to corresponding short video segments from the bore camera depicting the events.

Another advantage of the event extraction approach is that the original video may optionally be deleted immediately after the event is extracted. This could be beneficial as the events are de-identified, and so the events record would not implicate patient privacy.

In other embodiments disclosed herein, additional/other sensors, such as door switches, microphones, or accelerometers can be used to collect data during the imaging examination. One example of such sensors are compact Radar sensors, which can identify count/positions of persons in a room, and which might be considered less intrusive to patients and imaging technicians than mounting video cameras.

While described in the illustrative examples in terms of magnetic resonance (MR) imaging, the disclosed systems and methods can be used with any medical imaging modality that stores a machine log. Another example of the usefulness of the approach is in X-ray angiography, in which a C-arm imager is used in conjunction with a manually triggered contrast injector. While the angiography machine log typically stores timestamped entries for triggering of the contrast injector, it may not be apparent from the log file alone as to why the contrast is being injected (e.g., initial setup scout imaging, clinical imaging, etc.). Moreover, in some systems the contrast injector may not be in electronic communication with the X-ray C-arm imager controller, in which case the triggering events may not be recorded at all. The disclosed systems and methods would provide additional information that could enable more informative workflow performance assessment of angiography logs. In addition, the disclosed systems and methods can be used with other suitable imaging modalities, such as computed tomography (CT).

Figure 1:
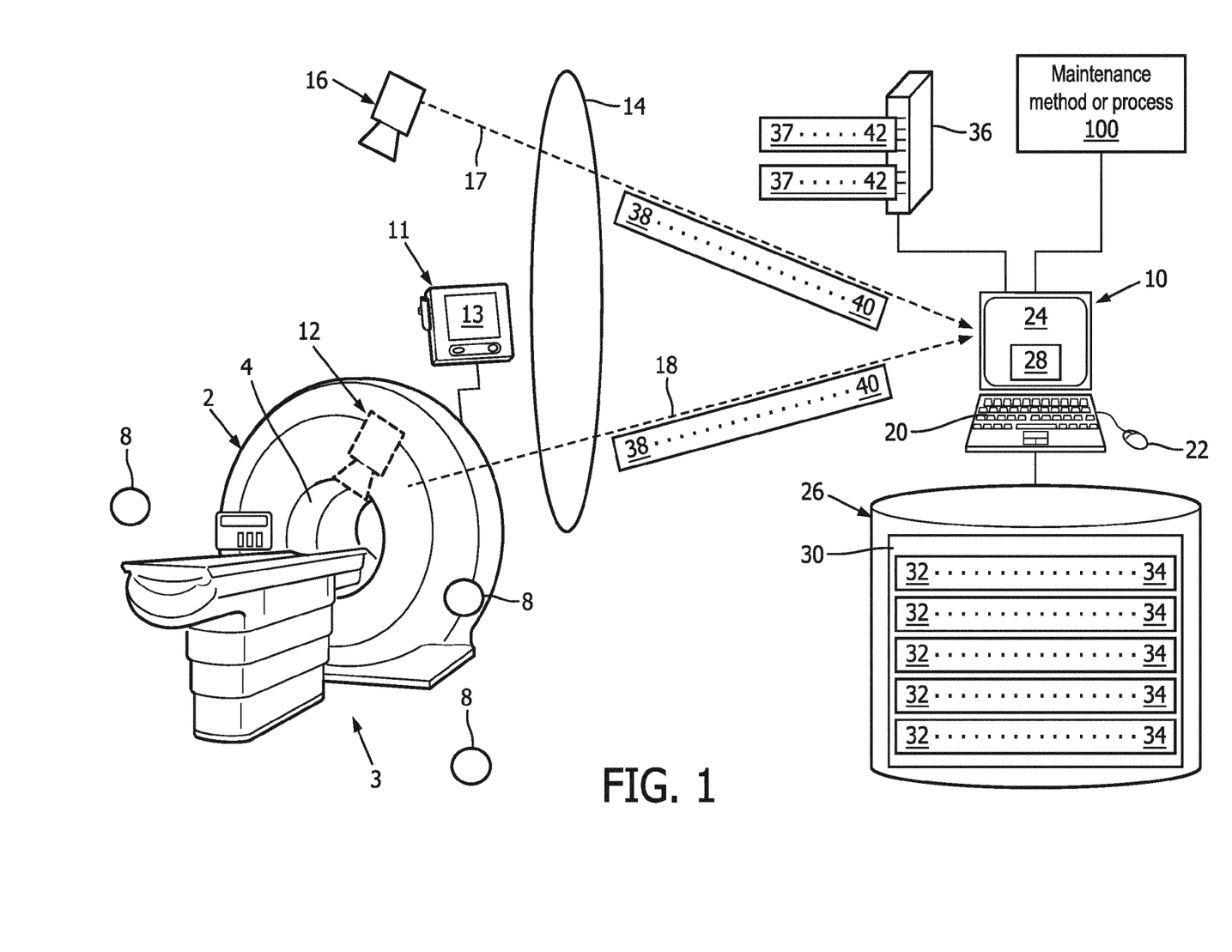
FIG. 1 diagrammatically shows an illustrative apparatus for maintaining a machine log of a medical imaging device in accordance with the present disclosure.

With reference to FIG. 1, an apparatus for a maintaining a machine log of a medical imaging device (also referred to as an image acquisition device, imaging device, and so forth) 2 located in a medical imaging device bay 3. The image acquisition device 2 can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; a C-arm angiography imager, or a medical imaging device of another modality. The imaging device 2 may also be a hybrid imaging device such as a PET/CT or SPECT/CT imaging system. While a single image acquisition device 2 in a single imaging bay 3 is shown by way of illustration in FIG. 1, more typically a medical imaging laboratory will have multiple image acquisition devices in respective imaging bays, which may be of the same and/or different imaging modalities. For example, if a hospital performs many CT imaging examinations and relatively fewer MRI examinations and still fewer PET examinations, then the hospital's imaging laboratory (sometimes called the "radiology lab" or some other similar nomenclature) may have three CT scanners, two MRI scanners, and only a single PET scanner. This is merely an example.

An imaging technician, or other operator controls the medical imaging device 2 via an imaging device controller 10. As shown in FIG. 1, the medical imaging device 2 and the imaging device controller 10 are disposed in the medical imaging device bay 3, while in other embodiments the imaging device and the imaging device controller can be disposed in separate locations (e.g., the imaging device in the imaging bay and the controller in an adjacent control room). Furthermore, it will be appreciated that over the course of an imaging procedure, other medical personnel may enter/leave the imaging bay 3. For example, a nurse and/or hospital orderly may assist in bringing the patient in, connecting/disconnecting ancillary medical equipment (e.g., an intravenous infusion pump), loading/unloading the patient into/from the imaging device 2, and/or so forth. In the case of an interventional imaging device 2, such medical personnel may include a surgeon who performs an interventional procedure (e.g., biopsy, catheterization, et cetera) on the patient while being guided by the imaging provided by the interventional imaging device. It will be further appreciated that various of these medical personnel and events may result in unexpected delays in the imaging workflow, and/or deviations from the standard imaging workflow. For example, there may be unexpected difficulties in loading or unloading of the patient, in connecting an infusion pump, or so forth. These events caused by or relating to human activity are conventionally not recorded in the machine log, or in the stored imaging examination results (e.g. images).

In some embodiments, to provide for contrast enhanced imaging, a contrast injector 11 is configured to inject the patient with a contrast agent. The contrast injector 11 is a configurable automated contrast injector having a display 13. The user (usually the imaging technician) loads a vial or syringe of contrast agent (or two, or more, vials of different contrast agent components) into the contrast injector 11, and configures the contrast injector 11 by entering contrast injector settings such as flow rates, volumes, time delays, injection time durations, and/or so forth via a user interface (UI) of the contrast injector 11. The UI may be a touch-sensitive overlay of the display 13, and/or physical buttons, keypad, and/or so forth. In a variant embodiment, the contrast injector 11 is integrated with the imaging device controller 10 (e.g., via a wired or wireless data connection), and the contrast injector 11 is controlled via the imaging device controller 10, including displaying the contrast injector settings in a (optionally selectable) window on the display of the imaging device controller 10. In such an embodiment, the dedicated physical injector display 13 of the contrast injector may optionally be omitted (or, alternatively, the dedicated physical injector display 13 may be retained and the contrast settings displayed at both the dedicated physical injector display 13 and at the imaging device controller 10). In general, the automated contrast injector 11 can employ any suitable mechanical configuration for delivery of the contrast agent (or agents), such as being a syringe injector, a dual-syringe injector, pump-driven injector, or so forth, and may include hardware for performing advanced functions such as saline dilution of the contrast agent, priming and/or flushing of the contrast injection line with saline, and/or so forth.

As used herein, the term "medical imaging device bay" (and variants thereof) refer to a room containing the medical imaging device 2 and also any adjacent control room containing the medical imaging device controller 10 for controlling the medical imaging device. For example, in reference to an MRI device, the medical imaging device bay 3 can include the radiofrequency (RF) shielded room containing the MM device 2, as well as an adjacent control room housing the medical imaging device controller 10, as understood in the art of MRI devices and procedures. In such embodiments, the medical imaging device 2 and the medical imaging device controller 10 can be in communication with each other (or with other separate locations) via a communication link 14, which typically comprises the Internet augmented by local area networks for electronic data communications. On the other hand, for other imaging modalities such as CT, the imaging device controller 10 may be located in the same room as the imaging device 2, so that there is no adjacent control room and the medical bay 3 is only the room containing the medical imaging device and the medical imaging device controller.

As diagrammatically shown in FIG. 1, a camera 16 (e.g., a video camera) is arranged to acquire a video stream 17 of a portion of the medical imaging device bay 3 that includes at least the area of the imaging device 2, and optionally may further include the imaging device controller 10 and/or the contrast injector 11. The camera 16 is also referred to herein as a bay camera, and is configured to acquire the video stream 17 of one or more medical personnel during the medical imaging examination (e.g., a number of medical personnel in the medical bay 3, a type of movement by medical personnel, an amplitude or magnitude of movement by medical personnel, and so forth). The video stream 17 acquired by the bay camera 16 is sent to the medical imaging device controller 10, e.g. as a streaming video feed received via the communication link 14. In embodiments in which the contrast injector 11 includes the dedicated physical injector display 13, the field of view (FOV) of the camera 16 may encompass the dedicated physical injector display 13, so that the content of the display 13 is captured in the video stream 17 and information on contrast injection events is thereby acquired. More commonly, the contrast injector 11 is in wired or wireless electronic communication with the medical imaging device controller 10 (e.g. via a USB cable or other physical electronic communication cable, or via Wi-Fi or another wireless communication link) and information on contrast injection events is thereby acquired by the imaging device controller 10.

Additionally or alternatively, a second camera 12 (e.g., a video) camera can be disposed in a bore 4 of the medical imaging device 2 (e.g., a bore camera), and is arranged to acquire another video stream 18 of the examination region from which the imaging device 2 acquires the medical images. In the illustrative example, the examination region is located inside the bore 4 of the medical imaging device 2. However, some other imaging modalities employ an open architecture in which the examination region is more open. For example, in a C-arm imager (not shown), a robotic C-arm has an x-ray tube disposed at one end of the C-arm and an x-ray detector disposed at the other end of the C-arm, with the arc of the C-arm positioning the detector to detect x-rays emitted by the x-ray tube. The patient undergoing imaging is disposed on an examination table located between the two ends, and hence in this architecture the examination region is the area "above" the examination table where the patient is disposed for imaging. In addition to capturing the examination region (and, hence, at least the portion of the patient disposed in the examination region), the second camera 12 may also optionally capture areas adjacent to the examination region (which may also be occupied by portions of the patient), a portion of the medical imaging device housing, and other areas such as the patient loading/unloading area. As the second camera 12 captures the examination region, it is positioned to observe patient movement within the bore, patient breathing, and so forth, during the acquisition of images). The video stream 18 acquired by the bore camera 12 is sent to the medical imaging device controller 10, e.g. as a streaming video feed received via the communication link 14.

In some embodiments, one or more sensors 8 can additionally or alternatively be disposed in the medical imaging bay 3. The sensor(s) 8 are configured to collect data related to the events corresponding to the movement of the patient or medical personnel, in addition to the number of people, in the medical imaging bay 3. In one particular example, the sensor(s) 8 can include a radar sensor configured to detect persons in the medical imaging bay 3 containing the medical imaging device 2. The radar sensor could be in addition to, or in place of, the video camera 16.

As shown in FIG. 1, the medical imaging device controller 10 comprises a workstation, such as an electronic processing device, a workstation computer, or more generally a computer, which is operatively connected to receive and present the video 17 of the medical imaging device bay 3 from the bay camera 16 and/or the video 18 of the patient from the bore camera 12. Additionally or alternatively, the medical imaging device controller 10 can be embodied as a server computer or a plurality of server computers, e.g. interconnected to form a server cluster, cloud computing resource, or so forth. The medical imaging device controller 10 includes typical workstation components, such as an electronic processor 20 (e.g., a microprocessor), at least one user input device (e.g., a mouse, a keyboard, a trackball, and/or the like) 22, and at least one display device 24 (e.g. an LCD display, plasma display, cathode ray tube display, and/or so forth). In some embodiments, the display device 24 can be a separate component from the medical imaging device controller 10. The display device 24 may also comprise two or more display devices. Optionally, the video 17 of the medical imaging bay 3 from the bay camera 16, and/or the video 18 of the patient from the bore camera 12, may be displayed in a window or windows on the display 24. The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 12, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the display device 24. The GUI 28 presents information pertaining to the control of the medical imaging device 2, such as configuration displays for adjusting configuration settings, an alert when the status information on the medical imaging examination satisfies an alert criterion of the imaging device 2, imaging acquisition monitoring information, presentation of acquired medical images, and so forth.

In embodiments discussed previously in which the contrast injector 11 is controlled via the medical imaging device controller 10, the contrast injector settings are displayed on the display 24 of the medical imaging device controller 10 (and, in such embodiments, the dedicated physical injector display 13 is optionally omitted). In embodiments in which the contrast injector 11 includes the dedicated physical injector display 13, the display 13 may be separately mirrored at the display device 24, for example being displayed in a separate window on the display device 24. The GUI 28 can also include one or more dialog screens, including, for example, an examination/scan selection dialog screen, a scan settings dialog screen, an acquisition monitoring dialog screen, among others.

A machine log 30 of the medical imaging device 2 can be stored in the non-transitory computer readable medium 26, and is made up of machine log entries 32 with corresponding timestamps 34. In some examples, the timestamp 34 can include a beginning timestamp and an ending timestamp.

The medical imaging device controller 10 can also include, or be in communication with via the communication link 14, a database 36 for storing images 37 acquired by the medical imaging device 2 during medical imaging examinations (e.g., a PACS database).

Conventionally, the machine log 30 records events generated by the operation of the medical imaging device 2, such as recording idle times, imaging scans/acquisitions, actions performed by various components of the medical imaging device 2, alarms generated by sensors of the medical imaging device 2 (for example recording an overheating alarm for a component or the like), and so forth. The machine log entries may optionally be hierarchical (i.e., shorter duration events may be "nested" within longer-duration events). Each machine log entry 32 has a timestamp 34. For an event without (or with negligible) duration, the timestamp 34 may be a single value. For example, a component overheating alarm may have a single timestamp when that alarm is triggered. For events with extended duration, the timestamp 34 may include begin and end timestamp components. For example, the machine log entry for an idle time event may include a "begin" timestamp indicating when the idle period began, and an "end" timestamp indicating when the idle period terminated. Machine log entries 32 may also be generated by ancillary components in electronic communication with the imaging device controller 10. For example, the contrast injector 11 may be in electronic communication with the imaging device controller 10 as previously discussed, and the machine log entries may include entries recording change to settings of the contrast injector 11, injection events, and so forth.

The machine log 30 may be used in various ways. In one common use scenario, the machine log 30 is uploaded to the vendor of the medical imaging device 2, and may be referenced by a remote service engineer endeavoring to diagnose a problem reported by the customer/imaging device operator. In a variant usage scenario, the uploaded machine log 30 is analyzed by artificial intelligence (AI) components for use in preventive maintenance situations, by proactively detecting problems (and scheduling them for resolution) before such problems manifest as a device shutdown or perceptible degradation in the quality of the acquired medical images. For example, the uploaded machine log 30 can be analyzed by the AI components to determine whether an imaging pixel of the medical imaging device 2 needs to be replaced based on the presence of artifacts in acquired images. In yet another usage scenario, the hospital may analyze the machine logs 30 to assess workflow efficiency of the imaging laboratory as a whole, and/or the workflow efficiency of individual imaging technicians and/or individual medical imaging devices. For example, the uploaded machine log 30 can be analyzed by the AI components to determine how many imaging sessions are completed in a certain time period (e.g., a number of examinations per hour, per day, and so forth).

The machine log entries 32 conventionally do not record actions by the patient, or by medical personnel. Yet, actions by the patient and/or medical personnel may provide a more comprehensive understanding of the machine log data. For example, an excessively long idle time log entry might be due to a slow work pace of the imaging technician; or, an excessively long idle time log entry might be due to difficulties in loading the patient into the imaging device (e.g., patient needs special assistance, patient is uncooperative, or so forth). Systematically excessively long idle times might also be due to ergonomic issues, such as suboptimal placement of the imaging device 2 in the imaging bay 3 which forces medical personnel to navigate obstacles in performing the patient loading/unloading. For example, the patient loading couch might be placed too close to a wall of the imaging bay 3, requiring a second person to assist in patient loading. As yet another example, in the case of a C-arm angiography device, contrast injector operations may be logged, but this information alone may be insufficient to track what stage of the angiography workflow is being performed. As disclosed herein, such ambiguities are remediated in the disclosed embodiments by way of the video 17, 18 which is mined to extract event annotations representing activities occurring during a medical imaging examination performed using the medical imaging device 2, and such event annotations are annotated to corresponding (based on time stamps) machine log entries. Optionally, the event annotations may additionally or alternatively be annotated to corresponding (again, by time stamp) images acquired by the medical imaging examination and stored in the PACS. The event annotations typically represent human activities, such as patient motion (of particular concern if it occurs during an image acquisition), patient breath holds (or failure to execute a breath hold), entry/egress of medical personnel into/from the imaging bay 3 (which, if occurring during patient loading or unloading, could indicate difficulties with the loading/unloading process), and/or so forth.

The medical imaging device controller 10 is configured as described above to perform a method or process 100 for maintaining the machine log 30 for the medical imaging device 2. The non-transitory storage medium 26 stores instructions which are readable and executable by the at least one electronic processor 20 (of the medical imaging device controller 10, as shown, and/or the electronic processor or processors of a server or servers on a local area network or the Internet) to perform disclosed operations including performing the method or process 100. In some examples, the method 100 may be performed at least in part by cloud processing.

Figure 2:
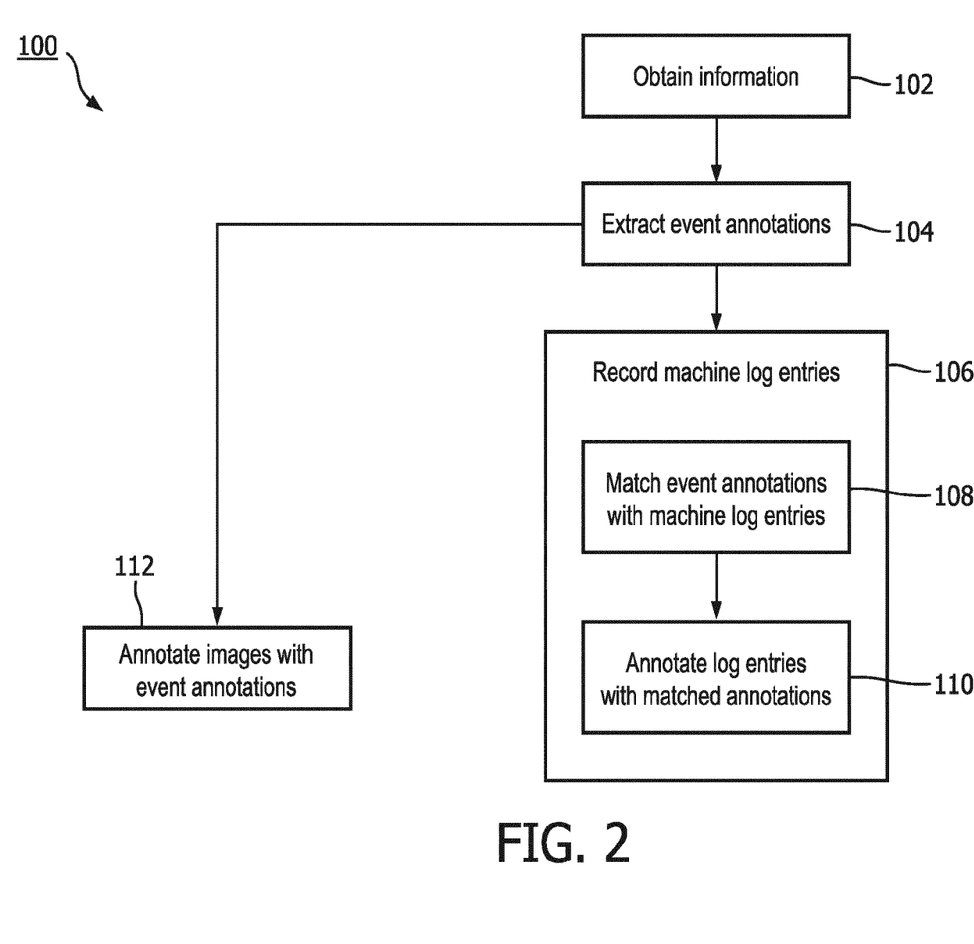
FIG. 2 shows an example flow chart of operations suitably performed by the apparatus of FIG. 1.

With reference to FIG. 2, and with continuing reference to FIG. 1, an illustrative embodiment of the method 100 is diagrammatically shown as a flowchart. The method 100 is performed over the course of a medical imaging examination performed using the medical imaging device 2. It will be appreciated that the medical imaging examination not only includes the acquisition of the images 37 but also pre-imaging procedures (e.g., entering the medical imaging bay 3, loading the patient into the medical imaging device 2, adjusting settings of the medical imaging device controller 10, movement about the medical imaging bay, and so forth), and post-imaging procedures (e.g., analyzing the images 34, unloading the patient, conversations between the patient and medical personnel, and so forth). In other words, the medical imaging examination begins when the patient and/or medical personnel enter the medical imaging bay 3 (or an adjacent room containing the medical imaging device controller 10), and ends then the patient and/or medical personnel exit the medical imaging bay/adjacent control room. (Machine log entries 32 may also be generated at time intervals between imaging examinations, for example if the imaging device 2 is not used at nighttime but a sensor 8 detects an overheating component at night then a time-stamped machine log entry for that alert is preferably generated).

At an operation 102, information about activities being performed during the medical imaging examination is obtained. In one example embodiment, this information is obtained by the sensor(s) 8. In other example embodiments, the information is obtained by the bore camera 12 and/or the bay camera 16 being positioned to image an examination region of the medical imaging device 2 and/or the medical imaging bay 3. For example, the information is obtained from the video stream 17 acquired by the bay camera 16 to capture activities of medical personnel in the medical imaging bay 3 (e.g., movement, number of personnel, and so forth) during the medical imaging examination. The information can also be obtained from the video stream 18 acquired by the bore camera 4 to capture activities of the patient (e.g., movement, breathing, and so forth) during the medical imaging examination.

At an operation 104, event annotations 38 are extracted from the video(s) 17 and/or 18 (or from the data collected by the sensor(s) 8). The event annotations 38 can include timestamps 40, and represent activities occurring during the medical imaging examination, or can include referring to the machine log 30.

At an operation 106, machine log entries 32 generated by the medical imaging device 2 are recorded or saved in the machine log 30. The machine log entries 32 can include, for example, at least sensor readings of sensors monitoring components of the medical imaging device 2, error codes generated by the medical imaging device, information on phases of the medical imaging examination performed using the medical imaging device, and so forth.

The extraction operation 104 can be performed in a variety of matters, as described in more detail below. In some example embodiments, the extraction operation 104 and the recording operation 106 work in tandem.

In one example embodiment of the extraction operation 104, a video segment from the bay video 17 acquired by the bay camera 16 and/or a video segment from the bore video 18 acquired by the bore camera 12 can be identified which depicts an activity (e.g., movement, determining a number of personnel in the medical imaging bay 3) during the medical examination. At least one event annotation 38 can be extracted which represents the video segment as one or more features extracted from the video segment. In a more particular example, when the depicted activity represents a human movement (either by the patient or medical personnel), the at least one event annotation 38 can indicated at least one of a type of the human movement, an amplitude of the human movement, a number of persons involved in the human movement, whether the human movement is by a patient undergoing the medical imaging examination or is by at least one person other than the patient in the imaging bay, and so forth. The formatting of the event annotations for human activity can be variously chosen. For example, in one approach each time a person is detected as entering (or exiting) the imaging bay 3, this event is detected. If the specific persons are not individually tracked, then this provides only information on the total number of persons in the imaging bay 3 at any given time. The annotation in this case could, for example, be of the form: "Bay occupied" with parameter values indicating the number of occupants, and timestamped with start and stop times. So, for example, event annotations could be formatted as follows:

Bay occupied, 1 occupant, start T1, end T2;
Bay occupied, 2 occupants, start T2, end T3;
Bay occupied, 1 occupant, start T3, end T4; . . . .

These event annotations record a sequence in which a first person enters at time T1, a second person enters at T2, one person (unknown which) leaves at T3, and the other person leaves at T4. On the other hand, if the specific persons are tracked within the bay 3 (for example, using sensors 8 in the form of RFID tag readers or the like), then the enter/exit events can be associated to specific persons, thus enabling more informative annotations such as:

Bay occupied, RFID #X, start T1, end T4;
Bay occupied, RFID #Y, start T2, end T3; ...

where here RFID #X and RFID #Y are unique identifiers (e.g. RFID tag numbers) of a first individual with RFID tag ID #X and a second individual with RFID tag ID #Y.

In another example embodiment of the extraction operation 104, at least one machine log entry 32 in the machine log 30 is detected during the medical imaging examination (e.g., during the recording operation 106). The machine log entry 32 can represent a detected activity during the medical imaging examination. One or more corresponding video segments of the detected machine log entry 32 can be identified in the bore video 18 and/or the bay video 17. This video segment(s) can be analyzed to detect the activity in the corresponding video segment(s). The at least one event annotation 38 representing the detected activity in the corresponding video segment can be extracted. In some examples, the detected machine log entry 32 can be updated by annotating the detected machine log entry with the extracted at least one event annotation 38 (and recorded or saved to the machine log 30). This approach can reduce the amount of the video 17, 18 that is analyzed to detect an event annotation representing a certain activity. For example, patient motion potentially leading to image blurring is only of concern during time intervals in which the patient is expected to remain stationary. Hence, the machine log 30 may be monitored to detect when an imaging sequence or image acquisition begins and ends, and the image analysis to detect patient motion is applied only to the video 18 acquired by the bore camera 12 during the time interval of the imaging sequence or image acquisition. If patient motion is detected by the analysis of the video 18, then the detected machine log entry 32 recording the imaging sequence or image acquisition (which is already recorded in the machine log 30) is updated by annotating the detected machine log entry with the extracted patient movement event annotation.

In a further example embodiment of the extraction operation 104, when the medical imaging device 2 includes the contrast injector 11 (i.e., the medical imaging examination is an angiography examination or otherwise utilizes an intravascular contrast agent), the recording operation 106 includes recording contrast injection operations performed by the contrast injector. In such embodiments, the extracting operation 104 includes identifying a contrast injection video segment of the bay video 17 and/or the bore video 18 which depicts a contrast injection operation performed by the contrast injector 11. The extraction process 104 in these embodiments entails reading the machine log 30 to detect the contrast injection operation, determining an injection time interval from timestamp(s) 34 of the corresponding machine log entry(-ies) 32, and then extracting the contrast injection video segment acquired during that time interval. Alternatively, if the contrast injector display 13 is visible in the bay video 17 and/or the bore video 18, then the contrast injection operation can be determined from those video segments. The contrast injection video segment can then be analyzed to extract an event annotation, such as a patient position event annotation indicating the patient and/or C-arm position during the contrast injection, which may be useful for identifying the type of angiography imaging being performed. Optionally, the analysis may further identify the type of angiography imaging from the patient and/or C-arm position during the contrast injection. The detected contrast injection machine log entry 32 (which, again, is already recorded in the machine log 30) is then updated by annotating the detected machine log entry with the extracted event annotation (e.g. the patient and/or C-arm position, or alternatively the type of angiography imaging determined based on this information).

In this embodiment, the identifying of the contrast injection video segment from the bay video 17 and/or the bore video 18 can include detecting a machine log entry 32 recording the contrast injection operation. The contrast injection video segment can be identified based on a time interval of the contrast injection operation as indicated by timestamps 34 of the machine log entry 32 recording the contrast injection operation. In another example, the timestamp 34 can be extracted from the detected machine log entry 32 to identify the contrast injection video segment. The at least one event annotation 38 representing the contrast injection operation in the video segment can be extracted.

One potential issue with recording the video 17, 18 relates to patient privacy. This is of particular concern if the machine log 30 is transferred to a third party, such as the vendor of the imaging device 2, who may be barred by applicable patient privacy regulations from having access to video of the patient undergoing the imaging procedure. In such cases, incorporating the video 17, 18 into the machine log 30 could create patient privacy concerns. Advantageously, the event annotations disclosed herein as being derived from the video 17, 18 generally do not contain personally identifying information (PII), and accordingly annotating these event annotations to the machine log 30 overcomes this potential concern. Optionally, the bay video 17 and/or the bore video 18 can be deleted after the event annotations 38 are extracted in order to further ensure patient privacy.

The recording operation 106 includes a matching operation 108 in which the extracted event annotations 38 with machine log entries 32 based on timestamps of the event annotations and the timestamps 34 of the machine log entries. For example, a match is determined if a time interval defined by the beginning and ending portions of the timestamp 40 of the event annotation 38 overlaps with the beginning and ending portions of the timestamp 34 of the machine log entry 32. In another example, a match is determined if the timestamp 40 of the event annotation 38 lies entirely within the interval of the timestamp 34 of the machine log entry 32. As previously noted, the timestamp matching may be implicitly performed in the process of extracting the event annotation. E.g., in the previous example of annotating an imaging sequence or acquisition with a patient movement event annotation, the time interval of the imaging sequence or acquisition is obtained from the initially recorded machine log entry for the imaging sequence or acquisition, and the video segment for this interval is then analyzed to extract any patient movement annotation(s), which are thus implicitly matched to the detected machine log entry recording the imaging sequence or acquisition.

The recording operation 106 also includes an annotating operation 110, in which the machine log entry 32 is annotated with the match event annotations 38. The annotated machine log entry 32 is recorded to the machine log 30 (or, as previously mentioned, an already-recorded machine log entry may be updated by adding the event annotation). In some examples, one or more annotated machine log entry(-ies) 32 can be retrieved from the machine log 30 and displayed on the display device 24, along with the matching event annotation 38.

In some embodiments, the method 100 includes an operation 112, in which the event annotations 38 are matched with one or more of the images 37 acquired by the medical imaging device 2 during the medical imaging examination. For example, the timestamps 40 of the event annotations 38 can be matched with a corresponding timestamp 42 of one or more images. In this example, the image 37 may have a single timestamp 42 (rather than a beginning and end portion, if the image is acquired in a fraction of a second), and a match occurs when the single timestamp 42 lies within the beginning and end portions of the timestamp 40 of the event annotation 38. Alternatively, if the image was generated by an extended imaging sequence (for example, in the case of a whole-body image acquired over an extended time interval over which the patient support moves the patient stepwise or continuously through the bore 4) then the match can be made if the timestamp of the motion occurs within the time interval of the extended imaging sequence. Similarly, if the acquired image is a cinematic (CINE) sequence capturing the inflow/washout of contrast agent over an extended time period, the match can be made if the timestamp of the motion occurs within the time interval of the CINE sequence acquisition. The images 37 can be annotated with the matched event annotation(s) 38, and displayed on the display device 24 with the matched event annotation (s) and/or stored in the PACS database 36. In addition, the event annotations 38 matched with the images 37 can be used to determine preventative maintenance issue (e.g., replacing an imaging pixel before it fails) or operational efficiency matters (e.g., determining how may imaging sessions are performed in a given time period) of the medical imaging device 2.

Figure 3:
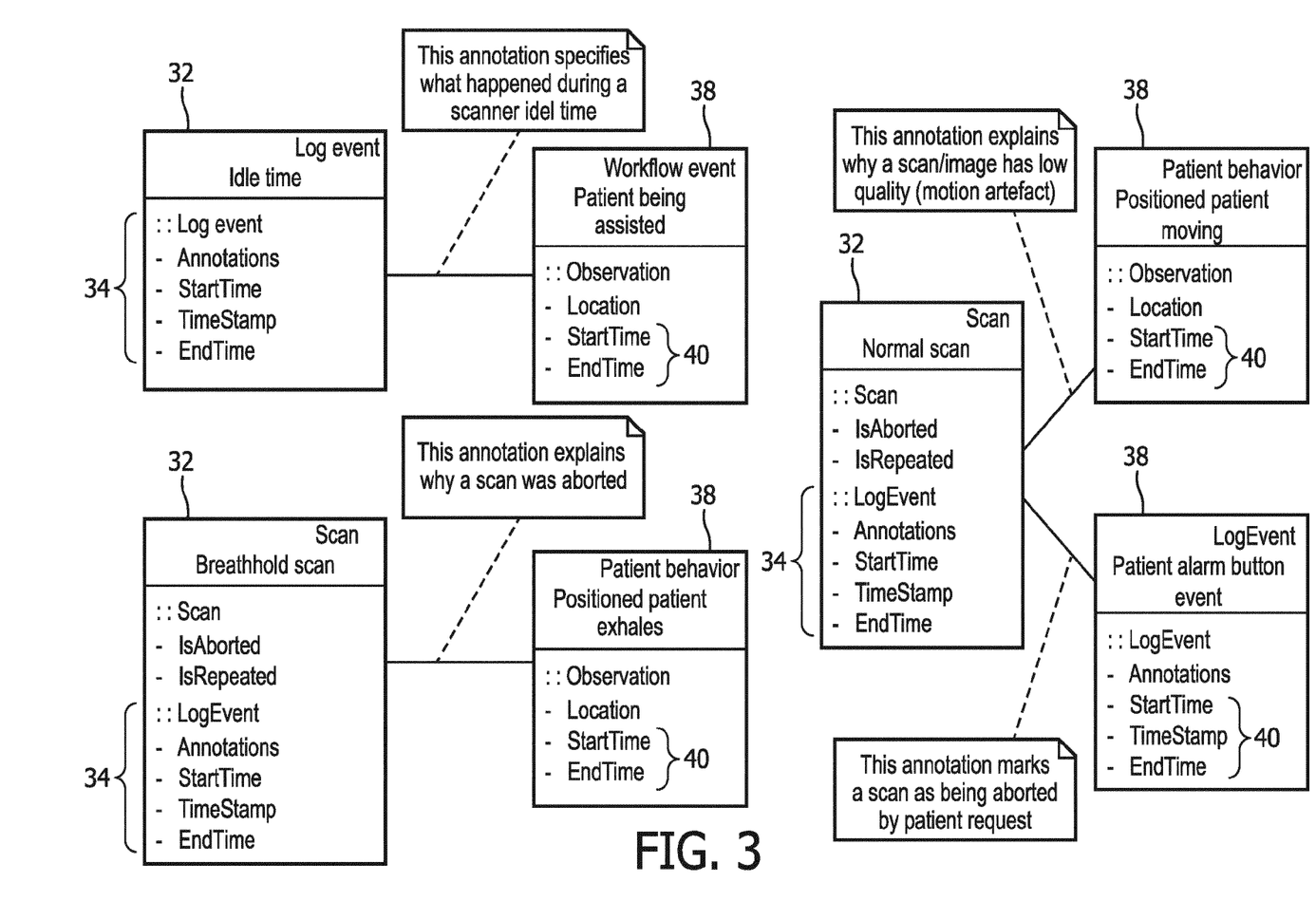
FIG. 3 shows examples of annotated machine log entries generated by the apparatus of FIG. 1.

FIG. 3 shows a graphical representation of an example of annotated machine log entries 32. A first machine log entry 32 is an "idle time" machine log entry. This machine log entry 32 shows a timestamp 34 (with beginning and end portions) with an event annotation 38 (e.g., a patient being assisted, which led to the idle time). The event annotation 38 includes the timestamp 34. A second machine log entry 32 is an "breathhold scan" entry, and also includes a timestamp 34 and an annotation 38 with a corresponding timestamp 40 for a "positioned patient exhales" event. A third machine log entry 32 is an "normal scan" entry, and also includes a timestamp 34, and multiple annotations 38 (with corresponding timestamps 40) for a "positioned patient moving" event, and a "patient alarm button" event. These are merely illustrative examples, and should not be construed as limiting.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium storing instructions readable and executable by at least one electronic processor to perform a method of maintaining a machine log for a medical imaging device, the method comprising:
acquiring a video of a patient during a medical imaging examination;
detecting an activity in the video occurring from the medical imaging examination;
extracting at least one event annotation representing the detected activity in the video, wherein the at least one event annotation represents a human-related activity;
analyzing the acquired video of the detected activity occurred during the medical imaging examination;
recording machine log entries in the machine log of the medical imaging device, wherein the machine log entries are generated by the medical imaging device and include at least one of 1) sensor readings of sensors monitoring components of the medical imaging device, 2) error codes generated by the medical imaging device, and 3) information on phases of the medical imaging examination performed using the medical imaging device;
matching the extracted event annotations with machine log entries based on timestamps of the event annotations and timestamps of the machine log entries; and
annotating the machine log entries with the matched event annotations.

2. The non-transitory computer readable medium of claim 1, wherein the method further includes:
matching one or more of the event annotations with one or more images acquired by the medical imaging device during the medical imaging examination;
annotating the one or more images with the matched one or more event annotations; and
at least one of:
displaying the annotated one or more images on a display device including displaying the matched one or more event annotations; and
storing the annotated one or more images in a database that stores images acquired during medical imaging examinations performed using the medical imaging device.

3. The non-transitory computer readable medium of claim 2, wherein the matching of the one or more of the event annotations with one or more images includes:
matching the timestamps of the event annotations with timestamps of the one or more images.

4. The non-transitory computer readable medium of claim 1, wherein the extracting of the event annotations includes:
identifying a video segment of the video which depicts an activity occurring during the medical imaging examination; and
extracting at least one event annotation representing the video segment as one or more features extracted from the video segment.

5. The non-transitory computer readable medium of claim 1, wherein the extracting of the event annotations includes:
identifying a video segment of the video which depicts a human movement; and
extracting at least one event annotation representing the human movement including an event annotation of indicating at least one of:
a type of the human movement;
an amplitude of the human movement;
a number of persons involved in the human movement, and
whether the human movement is by a patient undergoing the medical imaging examination or is by at least one person other than the patient in the imaging bay.

6. The non-transitory computer readable medium of claim 1, wherein the medical imaging device includes a contrast injector, the recording of the machine log entries includes recording contrast injection operations performed by the contrast injector, and the extracting of the event annotations includes:
identifying a contrast injection video segment of the video which depicts a contrast injection operation performed by the contrast injector; and extracting at least one event annotation which represents an imaging operation depicted in the contrast injection video segment.

7. The non-transitory computer readable medium of claim 5, wherein the identifying of the contrast injection video segment includes:
   detecting a machine log entry recording the contrast injection operation; and
   identifying the contrast injection video segment based on a time interval of the contrast injection operation as indicated by timestamps of the machine log entry recording the contrast injection operation.

8. The non-transitory computer readable medium of claim 5, wherein the method further includes:
   detecting a machine log entry recording a timestamp of the contrast injection operation;
   extracting the timestamp from the detected machine log entry;
   identifying, in the contrast injection video segment of the video, a contrast injection operation performed by the contrast injector at the extracted timestamp; and
   extracting at least one event annotation representing the detected activity in the corresponding video segment.

9. The non-transitory computer readable medium of claim 5, wherein the extracting of event annotations includes:
   detecting a machine log entry;
   identifying a corresponding video segment of the video of the detected machine log entry;
   analyzing the corresponding video segment to detect an activity in the corresponding video segment; and
   extracting at least one event annotation representing the detected activity in the corresponding video segment.

10. The non-transitory computer readable medium of claim 1, wherein the annotating includes:
    updating the detected machine log entry by annotating the detected machine log entry with the extracted at least one event annotation.

11. The non-transitory computer readable medium of claim 1, wherein the method further includes:
    deleting the video after the event annotations are extracted.

12. An apparatus for maintaining a machine log for a medical imaging device, the apparatus comprising:
    at least one video camera positioned to image an examination region of the medical imaging device; and
    at least one electronic processor programmed to:
      acquire a video of a patient during a medical imaging examination;
      detect an activity in the video occurring from the medical imaging examination;
      extract at least one event annotation representing the detected activity in the video, wherein the at least one event annotation represents a human-related activity;
      analyze the acquired video of the detected activity occurred during the medical imaging examination;
      record machine log entries in the machine log of the medical imaging device, wherein the machine log entries are generated by the medical imaging device and include at least one of 1) sensor readings of sensors monitoring components of the medical imaging device, 2) error codes generated by the medical imaging device, and 3) information on phases of the medical imaging examination performed using the medical imaging device;
      match the extracted event annotations with machine log entries based on timestamps of the event annotations and timestamps of the machine log entries; and
      annotate the machine log entries with the matched event annotations.

13. The apparatus of claim 12, wherein the at least one camera includes at least one of:
    a bore camera disposed in a bore of the medical imaging device, the bore camera being configured to acquire video of a patient during the medical imaging examination; and
    a bay camera disposed in the medical imaging bay, the bay camera being configured to acquire video of one or more medical personnel during the medical imaging examination.

14. A computer-implemented method of maintaining a machine log for a medical imaging device, the method comprising:
    acquiring a video of a patient during a medical imaging examination;
    detecting an activity in the video occurring from the medical imaging examination;
    extracting at least one event annotation representing the detected activity in the video, wherein the at least one event annotation represents a human-related activity;
    analyzing the acquired video of the detected activity occurred during the medical imaging examination;
    recording machine log entries in the machine log of the medical imaging device, wherein the machine log entries are generated by the medical imaging device and include at least one of 1) sensor readings of sensors monitoring components of the medical imaging device, 2) error codes generated by the medical imaging device, and 3) information on phases of the medical imaging examination performed using the medical imaging device;
    matching the extracted event annotations with machine log entries based on timestamps of the event annotations and timestamps of the machine log entries; and
    annotating the machine log entries with the matched event annotations.

15. The non-transitory computer readable medium of claim 1, further storing instructions readable and executable by at least one electronic processor to:
    retrieve, from the machine log, and display one or more of the machine log entries on a display device including displaying the matching event annotation.

16. The non-transitory computer readable medium of claim 1, wherein the method further includes at least one of:
    analyzing the machine logs to determine one or more preventative maintenance issues with the medical imaging device; and
    analyzing the machine logs to determine one or more operational efficiency matters with the medical imaging device.

17. The apparatus of claim 1, wherein the electronic processor is further programmed to:
    match one or more of the event annotations with one or more images acquired by the medical imaging device during the medical imaging examination;
    annotate the one or more images with the matched one or more event annotations; and
    at least one of:
      display the annotated one or more images on a display device including displaying the matched one or more event annotations; and store the annotated one or more images in a database that stores images acquired during medical imaging examinations performed using the medical imaging device.

18. The apparatus of claim 12, further including:
one or more sensors disposed in a medical imaging bay where the medical imaging examination occurs, the one or more sensors configured to collect data related to the events corresponding to the event annotations during the medical imaging examination.

19. The apparatus of claim 18, wherein the one or more sensors includes a radar sensor configured to detect persons in the imaging bay containing the medical imaging device.

\* \* \* \* \*